United States Patent [19]

Bohl et al.

[11] 4,134,289
[45] Jan. 16, 1979

[54] GAS SAMPLING SYSTEM HAVING A FLOW INDICATOR

[75] Inventors: Thomas L. Bohl, Madison; Robert E. Pocock, Highland Heights, both of Ohio

[73] Assignee: Bailey Meter Company, Wickliffe, Ohio

[21] Appl. No.: 848,004

[22] Filed: Nov. 3, 1977

[51] Int. Cl.$^2$ .............................................. G01N 1/24
[52] U.S. Cl. .................................... 73/23; 73/421.5 A
[58] Field of Search .................... 73/421.5 R, 421.5 A, 73/23; 340/239 F

[56] References Cited

U.S. PATENT DOCUMENTS

| 2,814,952 | 12/1957 | Ryant, Jr. et al. ............. 73/421.5 A |
| 3,457,787 | 7/1969 | Maatsch ......................... 73/421.5 A |

FOREIGN PATENT DOCUMENTS 756380  9/1956  United Kingdom ............... 73/421.5 A

*Primary Examiner*—S. Clement Swisher
*Attorney, Agent, or Firm*—Vytas R. Matas; Joseph M. Maguire

[57] ABSTRACT

A gas sampling system is provided having a combustibles detector and an oxygen detector supplied from a common sample line by their own individual aspirators. The aspirators are sized to allow the one aspirator to overpower the second aspirator whenever the common sample inlet is blocked a predetermined amount to thereby cause oxygen rich supply air to flow through the oxygen detector causing the oxygen detector to register an abnormal condition as an indication of blocked sample inlet.

10 Claims, 3 Drawing Figures

GAS SAMPLING SYSTEM HAVING A FLOW INDICATOR

BACKGROUND OF THE INVENTION

1. Field of the Invention

The present invention relates to gas sampling systems generally and particularly to closed loop gas sampling systems which return the sample to the area from which the sample was taken.

1. Description of the Prior Art

The control of various processes such as steel making as well as combustion control systems is dependent upon an accurate monitoring and analyzing of process gases such as combustion flue gases. These gases are normally analyzed for concentrations of various elements such as oxygen, carbon monoxide, carbon dioxide, sulfur dioxide, and other combustibles. Usually, individual analyzers are provided to measure the oxygen concentration as well as the combustibles concentration in the process gases.

The mentioned individual sampling systems usually had their own indicators for providing an indication of a plugged sample inlet line. Plugging occurs due to the dirty environment of the flue and such plugging must be taken into consideration to insure the continuous accurate operation of the analyzing system. The usual type of such flow indicator has been a pressure switch operating on negative pressure that is tied into the sampling system. Thus, as the inlet line is plugged up to a predetermined amount, negative pressure increases in the system eventually causing the switch to close a contact and indicate the malfunction.

The use of the aforementioned individual sampling systems for oxygen and combustibles resulted in a great duplication of parts and required more mounting space and installation time to be adapted to the duct. What was needed was a single sampling system which would check for both oxygen and combustibles level as well as providing a single indication of proper flow through the sample line.

SUMMARY OF THE INVENTION

The present invention solves the previously discussed problems of the prior art sampling systems as well as others by providing a single gas sampling system which is able to provide an indication of not only the oxygen content in the duct but also the combustibles level or content therein. To accomplish this, an oxygen detector as well as a combustibles detector are connected to a common sample inlet line communicating with the gases in the duct. The flue gases from the duct are individually drawn from this common sample line through both the oxygen detector and the combustibles detector by individual aspirator units connected to the oxygen detector and the combustibles detector which have their outlets exhausting into a common outlet line which feeds the sampled gases back into the duct.

In another embodiment of the present invention, the oxygen detector is utilized to provide an indication of a blocked condition in the sample inlet. To accomplish this, the two mentioned aspirators are sized so as to have the one aspirator overpower the second aspirator associated with the oxygen detector whenever the common sample line is blocked. The overpowering of the oxygen analyzer associated aspirator causes supply air to flow through the oxygen detector and the oxygen detector to then indicate an abnormally high oxygen level. This pins the indicator which signal may then be utilized to provide an alarm condition indicative of a blocked sample inlet.

From the foregoing it will be seen that one aspect of the present invention is to provide a closed loop sampling system detecting both oxygen and combustibles which will draw an exhaust sample gas from and to the same duct.

Another aspect of the present invention is to provide a sampling system which will establish a control signal indicative of a blocked sample line condition.

These and other aspects of the present invention will be more clearly understood after a review of the following description of the preferred embodiment of the invention when considered in conjunction with the accompanying drawings.

DESCRIPTION OF THE PREFERRED EMBODIMENT

Figure 1:
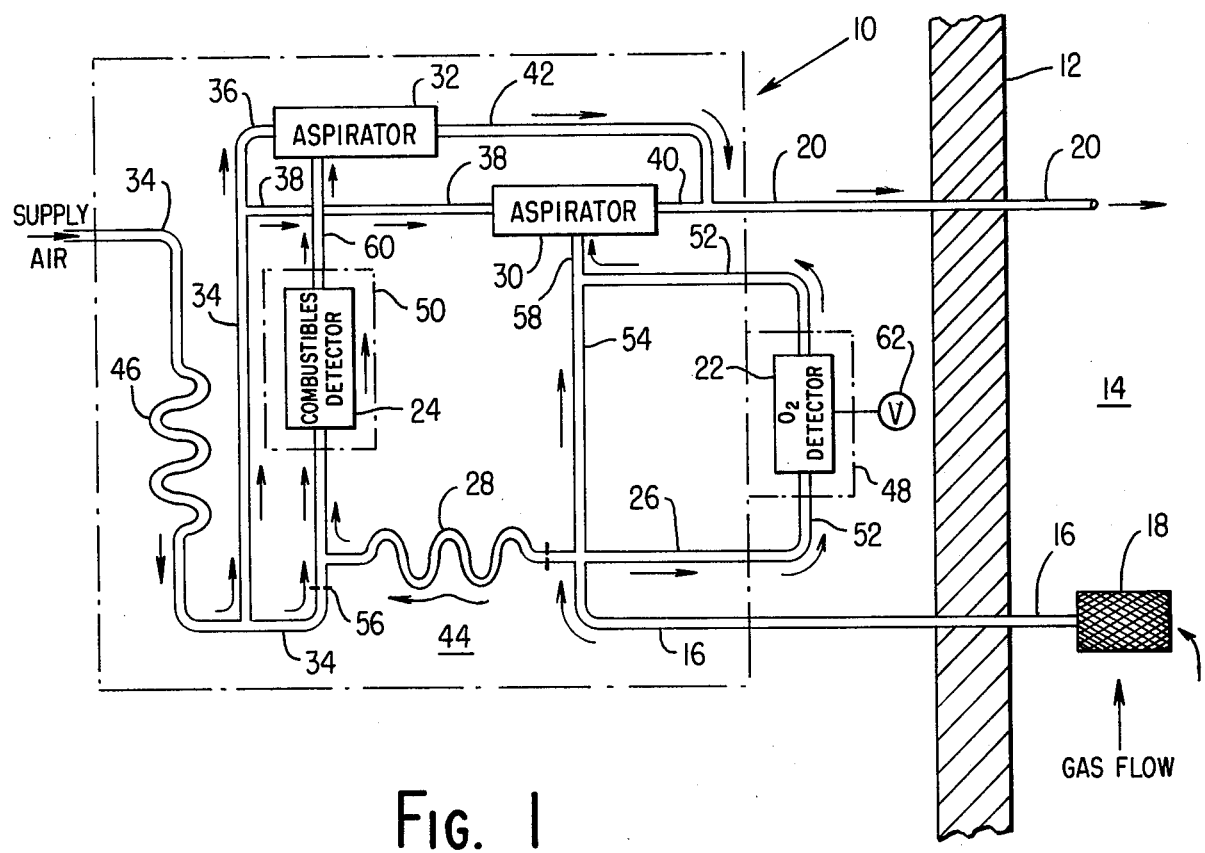
FIG. 1 is a schematic representation of the sampling system of the present invention showing sample gas flow under normal conditions.

Referring now to the drawing it will be understood that the showings therein are for the purposes of illustrating a preferred embodiment of the present invention and the invention is not limited thereto.

As may be best seen with reference to FIG. 1, a sampling system 10 is mounted to a duct or boiler wall 12 to draw process gas from the inside of a duct 14 and to exhaust it back thereto after analyzing the process gas for both oxygen and combustibles. The process gas sample is taken from an inlet line 16 extending through the duct wall 12 and having a filter 18 mounted to the end thereof. The analyzed sample is then exhausted back into the duct 14 through an outlet line 20 extending through the duct wall 12 downstream of the inlet line 16. This relative positioning of the inlet line 16 and the outlet line 20 is done to insure that the exhaust will not interfere with the inlet of a representative sample gas.

The gas sampling system 10 includes an oxygen detector 22 and a combustibles detector 24 both of which are connected to the inlet line 16 by respective oxygen detector inlet line 26 and combustibles detector inlet line 28. The sample gas from the mentioned inlet lines 16, 26, 28, is drawn through the oxygen detector 22 by an aspirator 30 while the sample is drawn through the combustibles detector 24 by an aspirator 32. The aspirators 30 and 32 are powered by supply air from a common supply air line 34 which has parallel trunk lines 36 and 38 supplying aspirators 32 and 30 respectively. The outputs of the aspirators 30 and 32 are exhausted to the exhaust line 20 by respective output lines 40 and 42 communicating with the exhaust line 20.

The aspirators 30 and 32 as well as the various inlet and outlet lines associated therewith are all enclosed in a heated block 44 which has an electric heater mounted therein (not shown) to maintain the temperature at approximately 400° F. well above the dewpoint of any flue gases or supply air to prevent condensation thereof. The supply air line 34 has a section 46 formed sinusoidally within the heated block 44 to delay the transport time of supply air to the aspirators to thereby insure that any supply air provided to the aspirators 30 and 32 will be sufficiently heated to prevent condensation. It should be noted that the inlet line 28 supplying gas to the combustibles detector 24 is similarly formed in a sinusoidal manner. The oxygen detector 22 is enclosed in a second heated block 48 mounted proximate to the heated block 44 and having a separate auxiliary heater (not shown) which maintains the oxygen detector at approximately 1500° F., the operating temperature of a Zirconium Oxide oxygen detector. The combustibles detector 24 is enclosed in yet another separate heated block 50 which also has its own separate heater (not shown) which maintains the combustibles detector at a temperature of approximately 800° F.

Turning next to the particular operation and description of the oxygen detector 22, it will be understood that the oxygen detector 22 is a well-known heated Zirconium Oxide oxygen detector which is sufficiently described in U.S. Pat. No. 3,960,500 entitled "GAS SAMPLING ANALYZING SYSTEM". The reader is referred thereto for further details of such oxygen detector. In operation, the aspirator 30 draws the flue sample from the duct 14 into itself through a pair of parallel lines 52 and 54 having the oxygen detector 22 located in line 52. The operation of the oxygen detector 22 in such a closed loop system and the function of the parallel line 54 is more than adequately described in the mentioned U.S. Pat. No. 3,960,500 and will not be recited herein for the sake of conciseness and readability.

The combustibles detector 24 may be any one of a number of well-known combustible detectors. An example of one such combustible detector is described in U.S. Patent application Ser. No. 724,682, filed Sept. 20, 1976, and entitled "COMBUSTIBLE GASES DETECTOR". The sample from the inlet line 16 is drawn through the combustibles detector 24 by virtue of aspirator 32 drawing the sample from inlet line 16 through combustibles inlet line 28 and into the combustibles detector 24. It will be noted that the combustibles detector 24 dilutes the sample from line 28 with an equal amount of supply air from sample line 34 prior to entering the combination into the combustibles detector 24. To insure that the dilution is in the 1 to 1 ratio of supply air to sample gas a flow regulator 56 is mounted in the supply air line 34 prior to the combustibles inlet line 28. The aspirator 32 then exhausts the sample and the dilution air along with its own supply air into exhaust line 42 which ultimately feeds into exhaust line 20 and back into the duct 14.

Turning now particularly to FIG. 1, it may be seen that the operation of the sampling system under normal operating conditions is as follows: the aspirator 30 as well as the aspirator 32 establish a negative pressure at their inlet lines 58 and 60 respectively which induces a flow of sample gas to inlet lines 26, 28, causing the sample to flow through the oxygen analyzer 22 and the combustibles detector 24. A bypass line 54 is also operated by the aspirator 30 to induce a greater quantity of sample from the inlet line 16 to thereby speed the reaction time of the oxygen detector 22 to a change in any conditions of the duct 14. Supply air is drawn through the regulator 56 and mixed with the sample gas from inlet line 28 into the combustibles detector 24.

Figure 2:
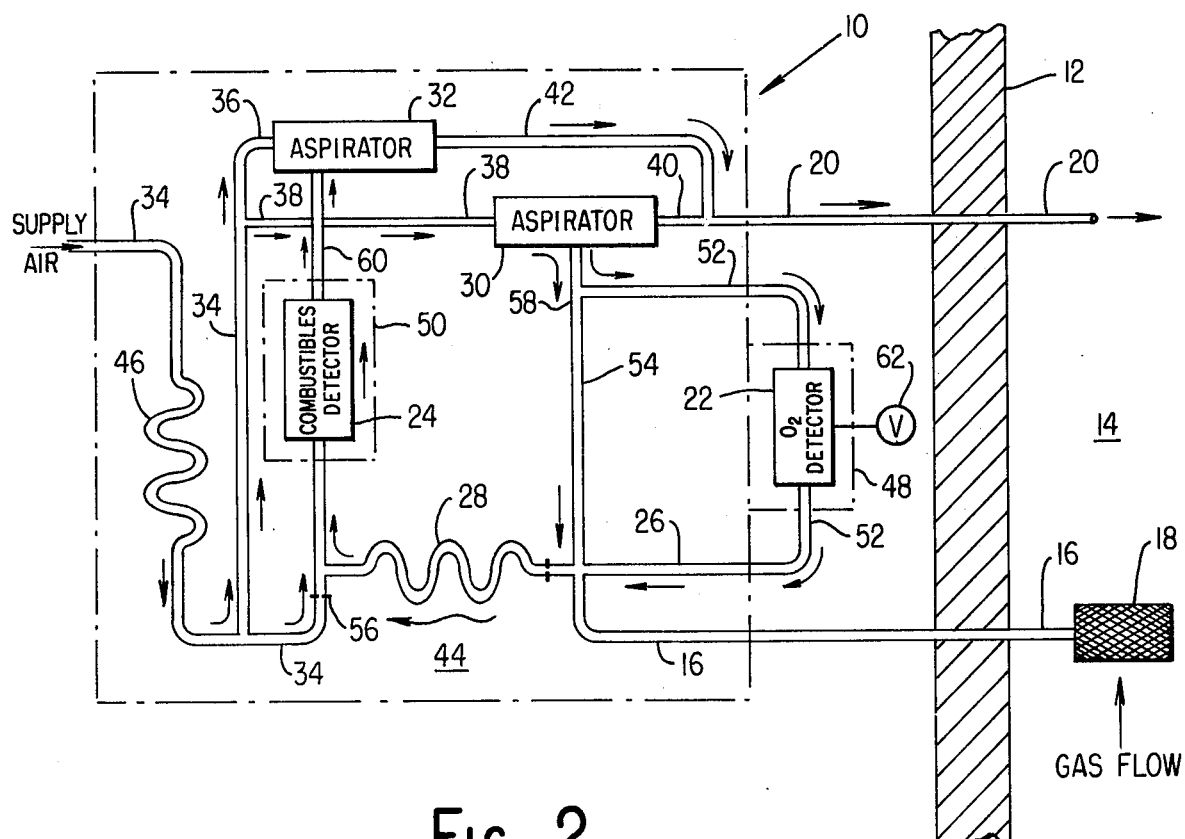
FIG. 2 is the schematic of FIG. 1 showing the modified flow of system gas during a blocked sample inlet condition.
Figure 3:
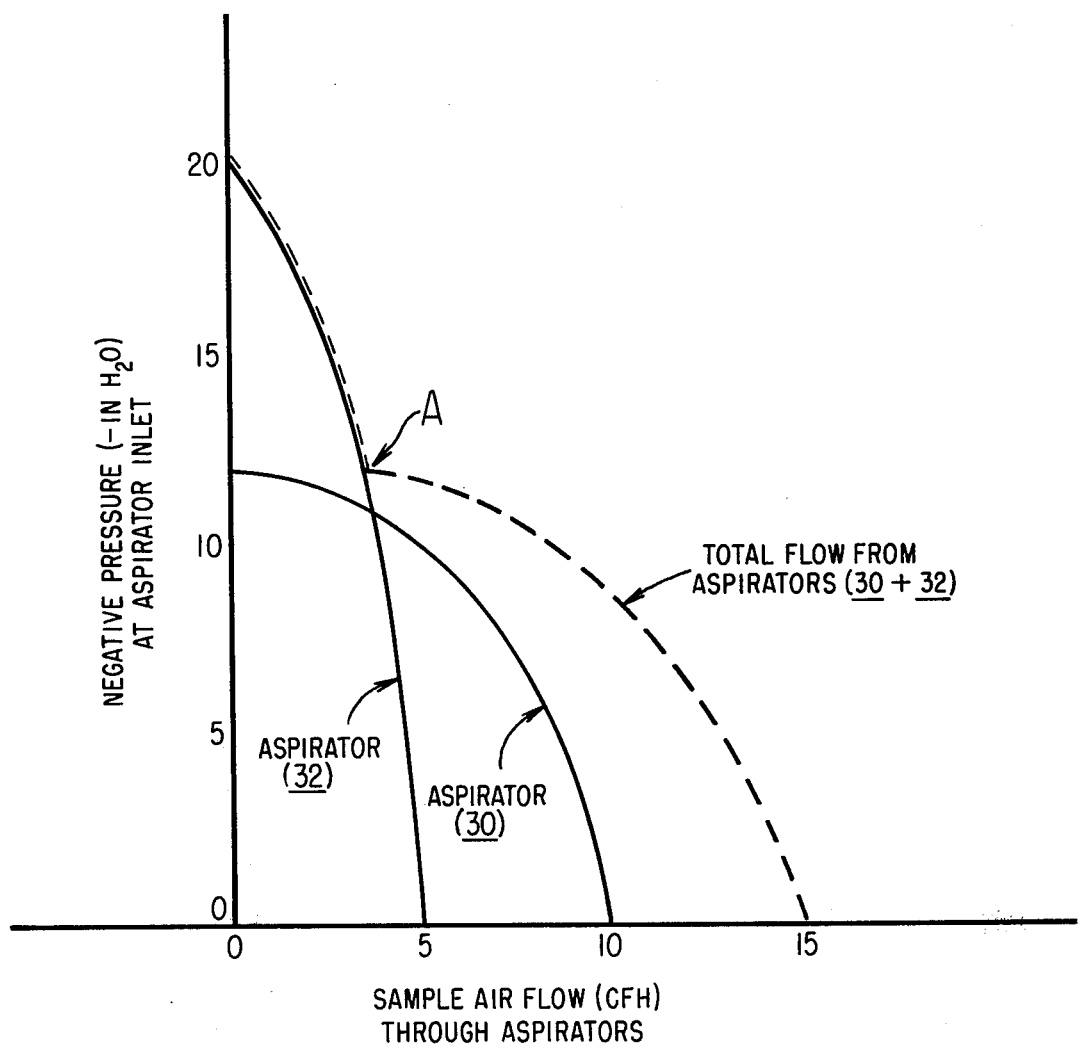
FIG. 3 is a graph indicating the flow characteristics of the pair of aspirators of the sampling system of FIG. 1.

As may be seen from FIG. 3, the aspirators 30 and 32 are sized so as to have aspirator 32 more efficient than the aspirator 30. The aspirator 32 is capable of developing a significantly higher negative pressure at its sample inlet 60 than the aspirator 30. This sizing becomes critical in providing a blocked inlet 16 indication in the sampling system 10. Referring now with particular emphasis to FIGS. 2 and 3, it will be seen that when the inlet line 16 becomes blocked due to a clogging of the filter 18 or the lodging of foreign particles in the actual inlet line 16, gas flow through the inlet line 16 will drop down to a level as indicated at point A on the chart of FIG. 3 to a point where there will be insufficient gas flow to supply both the aspirators 30 and 32. At this point, the aspirator 30 supplying the oxygen detector 22 will have insufficient negative pressure capability to draw any of the sample gas through itself and only the high negative pressure aspirator 32 will be able to draw any sample through itself. To compensate for the lack of sample gas, the aspirator 32 will now start drawing supply air from the aspirator 30 in a reverse direction from that shown in FIG. 1 through the oxygen detector 22, the bypass line 54, and into the combustibles detector supply line 28. Thus, we can see that now instead of sample duct gases being drawn through the oxygen detector 22, supply air originating at line 38 to feed the operation of the aspirator 30 will now be drawn through the sample inlet 58 of the aspirator 30 by the aspirator 32 and through the oxygen detector 22. Since the supply air is abnormally high in oxygen when compared to the oxygen content of the duct 14 gas, the oxygen detector 22 will start indicating this abnormally high oxygen content and will cause the voltmeter 62 which is calibrated to provide an indication of the oxygen content to be pinned or go off-scale. This off-scale reading of the indicator 62 can be used to provide a control signal indicative of a blocked inlet line 16 which can sound an alarm to indicate that the line must be cleaned either by replacing the filter 18 or backblowing supply air through it to dislodge any particles that may have become entrained in the inlet line 16.

From the foregoing it can be seen that the Applicants have provided a gas sampling system which indicates not only the oxygen content in a flue, but also the combustibles content therein. This sampling system furthermore utilizes the oxygen detector to establish a control signal indicative of a blocked inlet line 16 whenever the oxygen detector 22 goes out of range.

Certain modifications and improvements will occur to those skilled in the art upon reading this specification. As an example, individual exhaust lines could be run directly into the duct rather than a single manifolded exhaust line. It will be understood that all such improvements and modifications have been deleted herein for the sake of conciseness and readability but are intended to be within the scope of the appended claim.

What we claim are:

1. A gas analyzer for analyzing gases within a duct comprising:
   supply air means;
   inlet means mountable within the duct to draw a sample of the gases therein;
   an oxygen analyzing assembly connected to said inlet means; and
   aspirator means connected to said oxygen analyzing assembly for drawing gases from said inlet means through said oxygen analyzing assembly under normal conditions and drawing supply air from said supply air means through said oxygen analyzing assembly whenever said inlet means are blocked a predetermined amount.

2. A gas analyzer as set forth in claim 1 including a combustibles analyzing assembly connected to said inlet means and to said aspirator means to allow said aspirator means to draw gases from said inlet means through said combustibles analyzing assembly.

3. A gas analyzer as set forth in claim 2 wherein said aspirator means includes a first aspirator connected to said combustibles detector for drawing gases from said inlet means through said combustibles analyzing assembly and a second aspirator connected to said oxygen analyzing assembly for drawing gases from said inlet means through said oxygen analyzing assembly.

4. A gas analyzer for analyzing gases within a duct comprising:
   inlet means mountable within the duct to draw a sample of the gases therein;
   an oxygen analyzing assembly connected to said inlet means;
   a combustibles analyzing assembly connected to said inlet means;
   a first aspirator connected to said combustibles detector for drawing gases from said inlet means through said combustibles analyzing assembly;
   a second aspirator connected to said oxygen analyzing assembly for drawing gases from said inlet means through said oxygen analyzing assembly;
   an air supply connected to said first and second aspirators to power said aspirators; and
   said first and second aspirators being sized to allow said first aspirator to draw supply air through said oxygen analyzing assembly whenever said inlet means are blocked a predetermined amount.

5. A gas analyzer as set forth in claim 4 including an exhaust line connected to said first and second aspirators for exhausting the gases drawn through the oxygen and combustibles detecting assemblies back into the duct.

6. A gas analyzer as set forth in claim 5 wherein said inlet means includes a supply line having a single inlet mountable within the duct and a pair of branch lines connectable to the inlets of said oxygen analyzing assembly and said combustibles analyzing assembly.

7. An indicator assembly for providing an indication of a blocked inlet line of a gas analyzing assembly comprising:
   a source of gas to be analyzed;
   an inlet line connected to said gas source to convey said gas therethrough;
   a gas analyzing assembly connected to said inlet line;
   a supply air powered first aspirator assembly connected to said gas analyzing assembly to draw sample gas from said inlet line through said gas analyzing assembly;
   a second aspirator assembly connected to said inlet line to draw sample gas through itself under normal operating conditions and to draw supply air from said first aspirator assembly through said gas analyzing assembly whenever said inlet line is blocked a predetermined amount.

8. An indicator assembly as set forth in claim 7 wherein said gas analyzing assembly is an oxygen analyzing assembly for detecting oxygen content in flue gases.

9. An indicator assembly as set forth in claim 8 including a combustibles analyzing assembly connected between said second aspirator assembly and said inlet line.

10. An indicator assembly as set forth in claim 9 including a duct for conducting flue gases and an exhaust line connected to said first and second aspirator assemblies and wherein said inlet line and said exhaust line are connected to said duct.

* * * * *